United States Patent [19]

Pinckaers

[11] Patent Number: 4,890,616
[45] Date of Patent: Jan. 2, 1990

[54] ENERGY SAVING TECHNIQUE FOR BATTERY POWERED INDUCTOR

[75] Inventor: B. Hubert Pinckaers, Edina, Minn.

[73] Assignee: Medtronic, Inc., Minneapolis, Minn.

[21] Appl. No.: 788,379

[22] Filed: Oct. 18, 1985

Related U.S. Application Data

[63] Continuation of Ser. No. 624,873, Jun. 27, 1984, abandoned.

[51] Int. Cl.$^4$ .............................................. A61N 1/00
[52] U.S. Cl. ............................................... 128/419 R
[58] Field of Search ............. 128/1.5, 82.1, 419 F, 128/419 R, 421, 422; 320/21; 361/143, 155-156, 159; 328/78, 209; 331/86, 111-112, 112 FE; 318/130, 134

[56] References Cited

U.S. PATENT DOCUMENTS

| | | | |
|---|---|---|---|
| 3,158,791 | 11/1964 | Deneen, Jr. et al. | 361/156 |
| 3,893,462 | 7/1975 | Manning | 128/419 X |
| 4,223,367 | 9/1980 | Zappala | 361/156 |
| 4,256,116 | 3/1981 | Meretsky et al. | 128/421 |
| 4,454,558 | 6/1984 | Huddart | 361/156 |

Primary Examiner—William E. Ramm
Attorney, Agent, or Firm—Robert J. Klepinski; Joseph F. Breimayer

[57] ABSTRACT

A battery-powered medical treatment inductor coil generates a pulsed current inducing a magnetic field in the inductor coil for interaction with the patient's body. At the end of a pulse, the magnetic field collapses and an energy recovery circuit returns the energy in the collapsing field to the battery to reduce its average drain thus prolonging battery life.

5 Claims, 2 Drawing Sheets

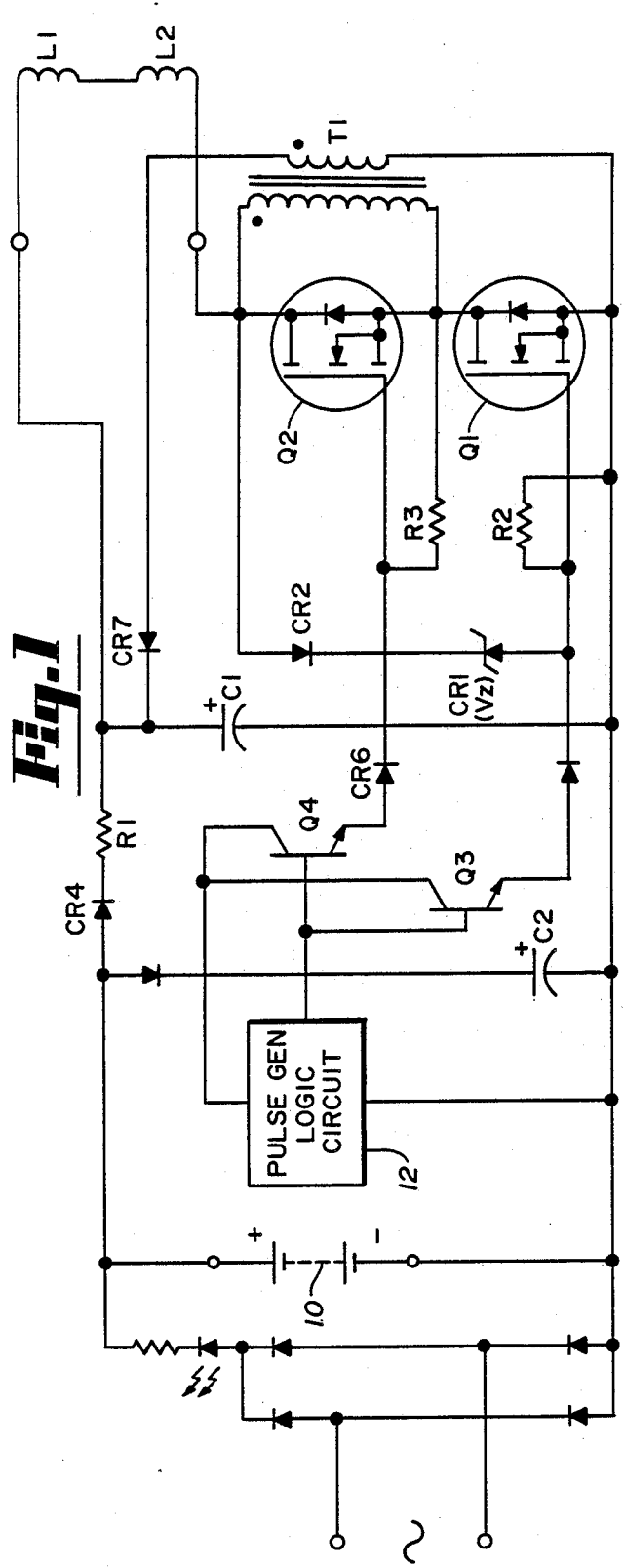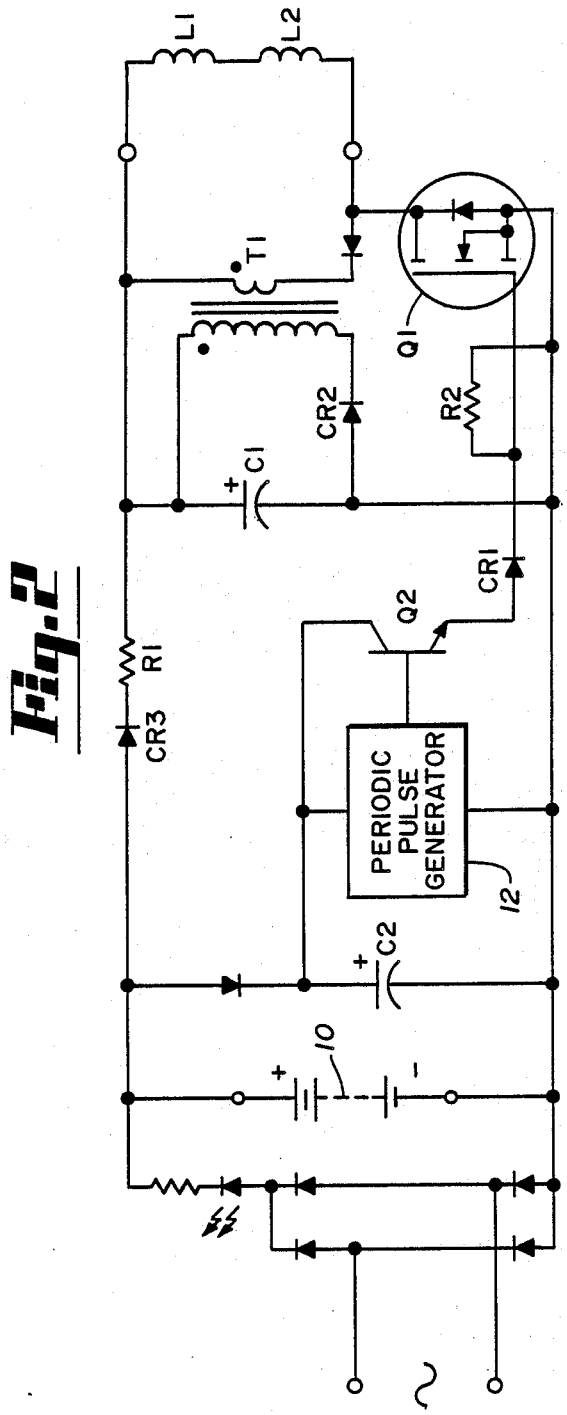

ENERGY SAVING TECHNIQUE FOR BATTERY POWERED INDUCTOR

This application is a continuation of U.S. patent application Ser. No. 624,873, filed June 27, 1984, now abandoned.

BACKGOUND OF THE INVENTION

1. Field of the Invention

The present invention relates to energy saving circuits for battery powered medical devices using inductor treatment coils.

2. Prior Art

The healing of bone fractures with the assistance of electrical stimulation is an established medical protocol. Experiments in such treatments have been conducted since Michael Faraday demonstrated the effefts of the induction coil. The experiments have involved invasive systems with implanted electrodes and external systems which couple with the patient's body by inductive or capacitive means. Inductive stimulation systems involve placing inductor coils adjacent the patient's skin surrounding an area of which healing is needed. The common arrangement is to use a pair of coils in a Helmholtz flux-aiding relationship. The devices were commonly molded into a cast. Normal alternating current from the patient's house supply was used to power the device. Treatment was commonly applied during the night when the patient was sleeping.

Because of the inconvenient nature of this AC line power attachment, a battery powered portable bone stimulator is desired. In any portable battery powered unit, the size and weight of the batteries is a limiting factor. For this reason, the battery should preferably be rechargeable and of minimum weight and size consistent with the number of hours of uninterrupted service required. It is important to minimize the size and weight of the unit, while allowing enough power to provide proper treatment. In the prior art, portable units were only used on small bone fractures such as in the wrist, because of this size limitation.

What is needed in the art is means for minimizing the use of energy in a bone stimulating device so that the stimulating device can be made light enough and small enough to be worn by the patient.

SUMMARY OF THE INVENTION

The present invention involves a battery source of power, means for temporarily storing power, circuit means for generating stimulating pulses utilizing the means of storing power, and a medical treatment inductor coil for interaction with the body of a patient. The invention includes means for recovering power during collapse of the magnetic field of the coils as current decreases and for directing such power to the means for temporarily storing power.

In one embodiment, energy from batteries is stored in a capacitor. The capacitor is discharged to provide a high current pulse for driving the coil. Energy from this current flow is stored as inductive energy in the coil when current is increasing. When energy from the capacitor is stopped, current in the coil decreases and the magnetic field collapses. The released inductive energy is captured and stored in the capacitor as electrical energy for a successive current pulse to the coils.

Various embodiments are applicable to differing types of circuits which provide a treatment pulse from the coils either during the driven portion of a waveform or during the fly-back portion in which coil current is decreasing.

BRIEF DESCRIPTION OF THE DRAWINGS

FIG. 1 is a schematic drawing of a circuit embodying the present invention, partially disclosed in block diagram form;

FIG. 2 is a schematic drawing of an alternative circuit embodying the present invention, partially disclosed in block diagram form;

DETAILED DESCRIPTION OF THE PREFERRED EMBODIMENT

Figure 3:
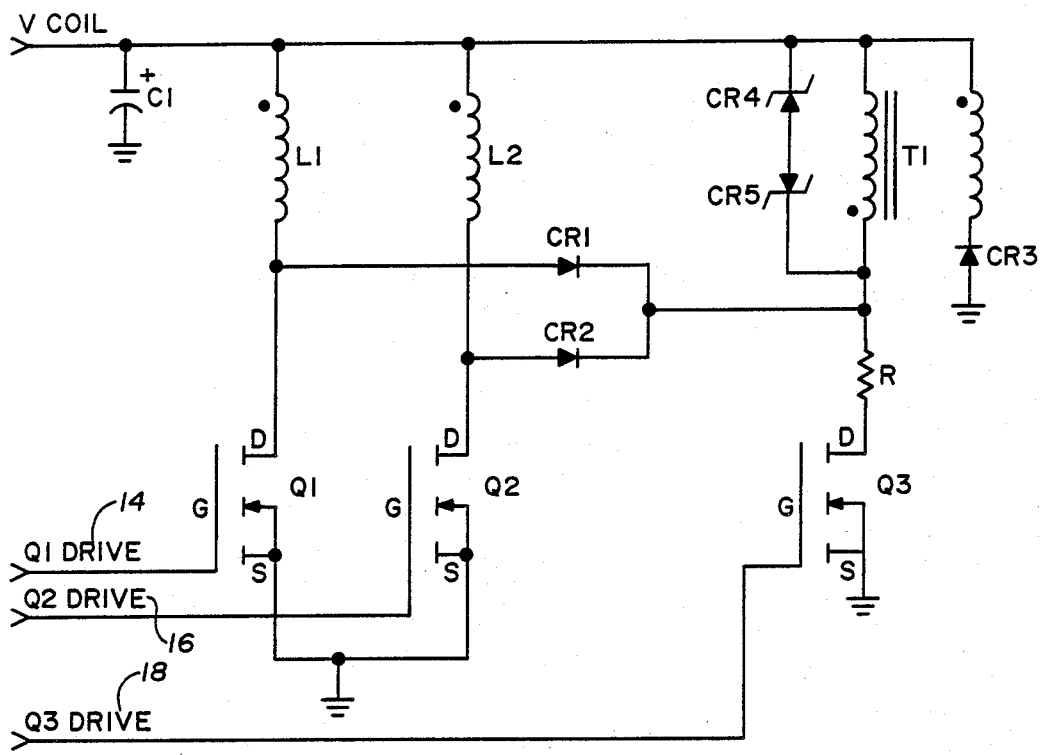
FIG. 3 is a schematic drawing of an alternative circuit embodying the present invention, partially disclosed in block diagram form.

The first embodiment illustrated in FIG. 1 includes battery 10 which is charged by an AC power source by means of a rectifier bridge and limiting resistor. Battery 10 charges capacitor C1 through diode CR4 and resistor R1. Capacitor C1 provides the relatively high current pulse needed for building a magnetic field for inductive stimulation. Battery 10, without acting through capacitor C1, is unable to furnish this high pulse.

A pulse of current is provided to coils L1 and L2 when power FETs Q1 and Q2 are switched on. A high current pulse is provided to the coils from capacitor C1. Current in coils L1 and L2 increases in a ramp like manner. When current in the coils L1 and L2 reaches a desired value, coils L1 and L2 are suddenly switched off by power FETs Q1 and Q2. At this instant, energy provided by capacitor C1 is stored in the magnetic field of coils L1 and L2. The switching of current to coils L1 and L2 is controlled by a pulse generator logic circuit 12. Circuit 12 emits bursts of control signals which controls the current to coils L1 and L2.

Pulse generator logic circuit 12 works at low voltage logic drive levels. Transistors Q3 and Q4 buffer this low energy drive pulse, which causes a charging pulse of coils L1 and L2, and increase the drive capability for driving power FET transistors Q1 and Q2. This is done through diodes CR5 and CR6 respectively.

During the driven portion of a waveform produced by pulse generator logic circuit 12, transistors Q1 and Q2 are on. In this state, capacitor C1 discharges through coils L1 and L2, providing the therapeutic effect of the patient.

Circuitry embodying the present invention recovers a significant portion of stored inductive energy from coils L1 and L2 as the magnetic field collapses. In this embodiment, the magnetic field decreases rapidly and there is a high fly-back voltage.

When the driven portion of the waveform terminates, coils L1 and L2 discharge stored inductive energy as the magnetic field collapses. This starts a current flowing in the primary coil of transformer T1, which is a light-weight small transformer. This induces a current in the secondary coil of transformer T1 which is provided through diode CR7 to charge capacitor C1. This charge represents recovered energy from coils L1 and L2 that would have normally have been dissipated in heat and thus C1 recovers part of the energy it lost when driving the coils L1 and L2. When coil current in coils L1 and L2 is increasing, both transistors Q1 and Q2 are conducting. When coil current in coils L1 and L2 is decreasing, only transistor Q1 conducts due to conduction in Zener diode CR1.

The circuit thereby returns the stored inductive energy to capacitor C1 so that the average current supplied by capacitor C1 is diminished. Therefore, the current draw from battery 10 is diminished. This results in longer periods between recharging of battery 10. In this embodiment, the therapy pulse is provided during the rapid current decrease during the fly-back period.

In the embodiment illustrated in FIG. 2, the circuit is designed such as that the desired stimulation signal is induced during the driven period of the waveform. That is, when the coil current is increasing, the therapy pulse is provided. In this embodiment, the magnetic field in coils L1 and L2 is allowed to collapse more slowly. The choice of embodiments relates to which type of therapy pulse is desired.

The embodiment illustrated in FIG. 2 includes the same recharging source, battery 10, and pulse generator 12 which operate in a manner similar to the embodiment of FIG. 1. In this embodiment, however, there is only one control transistor Q2 and one power FET transistor Q1. The Zener diode is not used. This avoids the power dissipation through the second power FET. When transistor Q2 is turned on, it provides a signal through diode CR1 to turn on power FET transistor C1. This energizes coils L1 and L2 with power from capacitor C1, which operates in the same manner as in the previously described embodiment.

When transistor Q1 is turned off, coils L1 and L2 generate a voltage which gives rise to a current through the primary coil of transformer T1. This induces a current in the secondary which charges capacitor C1 which is connected in series with diode CR2. Because power FET Q1 is fully off during the discharge cycle, more energy is returned through transformer T1 to capacitor C1.

Another alternative embodiment, as illustrated in FIG. 3, involves separate pulse generation circuits 14 and 16 which are connected to the gates of FET transistors Q1 and Q2 respectively. The source terminal of both transistors Q1 and Q2 is connected to ground and their drains are connected to one side of coils L1 and L2 respectively. The opposite side of each coil L1 and L2 is connected to capacitor C1. Capacitor C1 is charged by voltage $V_{coil}$ in a manner similar to the charging process of the other embodiments illustrated.

Coils L1 and L2 are connected through diodes CR1 and CR2 respectively to one side of the primary of transformer T1, and parallel with resistors R1 and the drain of FET transistor Q3. The source of transistor Q3 is connected to ground and its gate is connected to drive circuitry 18. The other side of the primary of transformer T1 as well as the secondary of transformer T1 is connected to capacitor C1. Connected in parallel to transformer T1 is a pair of Zener diodes CR4 and CR5 positioned in opposite polarity.

Initially, transistors Q1 and Q2 are driven on simultaneously. These transistors remain on during the driven portion of the waveform. This portion of the waveform tends to discharge capacitor C1 and stores inductive energy in coils L1 and L2.

At the end of the driven portion of the waveform, transistors Q1 and Q2 are turned off. This induces a fly-back voltage from the lower end of coils L1 and L2 with respect to ground. This voltage attempts to go very high, but diodes CR1 and CR2 begin to conduct at the same time the current starts to flow into the primary of transformer T1. When power FETs Q1 and Q2 are turned off, the stored inductive energy in coils L1 and L2 attempts to keep current flowing in coils L1 and L2. Therefore, coils L1 and L2 generate a voltage such that their lower ends are positive with respect to their upper ends. This voltage, which appears across FETs Q1 and Q2 in their nonconductive state, is placed across the primary winding of transformer T1 such that the end with the polarity dot in FIG. 3 is positive.

This primary voltage is transformed down by the secondary winding of transformer T1 to just exceed the voltage at that time across capacitor C1, so capacitor C1 can be charged through diode CR3.

Transformer T1 serves as a controlled clamping device which inverts a voltage back to the proper level for charging capacitor C1. The transformer controls the width of the fly-back pulse relative to the driven pulse. Fly-back amplitude is maintained proportional to amplitude of the driven pulse.

Transistor Q3 serves to drive the primary of transformer T1 during a different portion of the waveform. Transistor Q3 keeps the drive to transformer T1 balanced so that the volt/time integral driven into the primary of transformer T1 has a net value of zero. This keeps transformer T1 from saturating, especially during bursts of pulses.

A transformer is more likely to saturate in a burst pattern of pulses because the pulses are spaced so closely together. When the pulses are closely spaced, it has been found to be more efficient to drive the transformer during the driven portion of the pulse. Even though there is little actual current flow during the driven portion, the transformer T1 does have a voltage supplied. The volt/time integral applied to the primary of transformer T1 is cancelled by an almost equal volt/time integral in the opposite direction during the fly-back portion of the pulse. This allows the circuit to use a small transformer T1. Without this feature, transformer T1 would have to be much larger and bulkier.

Diodes CR4 and CR5 clamp the fly-back transient voltage so that it does not become excessively high. Too high a voltage could exceed the voltage breakdown capability of output drive transformers Q1 and Q2. Diodes CR4 and CR5 are Zener transient suppressors.

Figure 4:
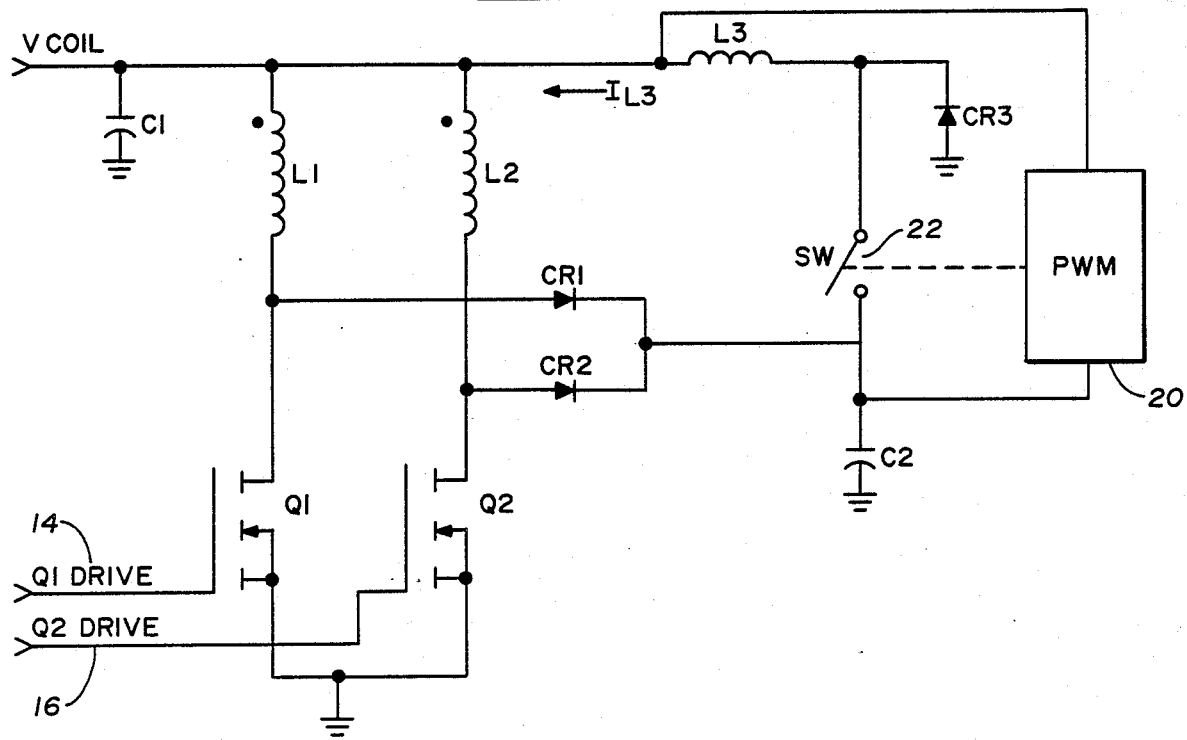
FIG. 4 is a schematic drawing of an alternative circuit embodying the present invention, partially disclosed in block diagram form.

Another alternative embodiment, as illustrated in FIG. 4, does not use a transformer. Instead, the circuit employs coil L3 and capacitor C2. This allows the circuit to be smaller to save weight and size in the therapy device.

This embodiment includes a pulse width modulator 20 and a switch 22. Switch 22 runs independently of the driven pulse and fly-back pulse at a frequency preferably 20 KHz to 100 KHz, which is a much higher frequency than the treatment pulse frequency. The higher the switch frequency, the lower the peak recovery currents will be. With lower peak currents, a smaller inductor L3 is usable.

Coil L3 absorbs the difference in voltage between the voltage in capacitor C2, which is charged during the fly-back period with energy that has been stored in coils L1 and L2, and supply capacitor C1. The capacitance of capacitor C2 is governed by how rapidly the current in coils L1 and L2 decreases. In general, the capacitance of capacitor C2 is far less than that of capacitor C1. The difference in voltage is absorbed by coil L3 which stores energy when switch 22 is closed. Coil L3 gives up that stored inductive energy to capacitor C1, through diode CR3, when switch 22 is opened.

The rest of the circuit involving coils L1 and L2 is similar to the embodiment of FIG. 3 except that the diodes CR1 and CR2 are connected to ground through capacitor C2.

Coil L3 is used to smooth the recovery current which is indicated as $I_{L3}$ in FIG. 4. Without coil L3, the current will rise sharply when switch 22 has closed because charge would transfer from capacitor C2 back to capacitor C1, in a relationship where capacitor C2 is at approximately three times the voltage of capacitor C1. There would be a rush of current and a power loss across switch 22. Coil L3 keeps changes in current at coil L3 down and prevents a sudden in-rush of excessive current to capacitor C1.

When switch 22 is opened, diode CR3 continues to conduct current through coil L3 into capacitor C1 due to stored energy in inductor L3, so there is actually a continuous flow of current through coil L3. When switch 22 is closed, the current rises in a ramp-like manner. When switch 22 is open, diode CR3 conducts and the current begins to drop. With modulator 20, the actual current $I_{L3}$ is regulated, as well as voltage across capacitor C2.

While the energy saving technique of the present application is illustrated by particular embodiments, it is to be understood that they are merely illustrative.

What is claimed is:

1. Medical treatment apparatus comprising:
   (a) means for applying an electromagnetic field to a treatment site of a patient;
   (b) means responsively coupled to said applying means for generating a flow of current and a subsequent flow of current in said applying means;
   (c) means responsively coupled to said generation means for interrupting said flow of current in said applying means;
   (d) means responsively coupled to said applying means for storing excess energy present in said applying means upon interruption of said flow of current by said interrupting means; and
   (e) means responsively coupled to said generating means and said storing means for enabling said generating means to utilize said excess energy for generating said subsequent flow of current.

2. Medical treatment apparatus according to claim 1 wherein said applying means further comprises an output stimulating coil coupled to said generating means.

3. Medical treatment apparatus according to claim 1 wherein said storing means further comprises a capacitor coupled to said generating means.

4. In a medical treatment device having a pulse generator and an output stimulating coil coupled to said pulse generator wherein said pulse generator causes a current to flow through said output stimulating coil in such a manner as to electromagnetically induce current to flow at a treatment site of a patient, the improvement comprising:

means responsively coupled to said pulse generator for interrupting said flow of said current through said output stimulating coil;
   means responsively coupled to said output stimulating coil for storing excess energy present in said output stimulating coil upon an interruption of said current by said interrupting means; and
   means responsively coupled to said storing means and said pulse generator for directing said excess energy to said pulse generator for generation of a subsequent flow of current.

5. A medical treatment device according to claim 4 wherein said storing means further comprises a capacitor.

* * * * *